United States Patent [19]

Olson

[11] 4,174,816
[45] Nov. 20, 1979

[54] STERILE SURGICAL CORD AND TUBE RETRACTOR

[75] Inventor: Leslie C. Olson, Minneapolis, Minn.

[73] Assignee: The Regents of the University of Minnesota, Minneapolis, Minn.

[21] Appl. No.: 367,640

[22] Filed: Jun. 6, 1973

[51] Int. Cl.² .......................................... B65H 75/36
[52] U.S. Cl. ................................... 242/47.5; 433/78
[58] Field of Search ................. 242/47.5, 55.01; 32/22

[56] References Cited

U.S. PATENT DOCUMENTS

| | | | |
|---|---|---|---|
| 1,384,153 | 7/1921 | Roos | 242/47.5 |
| 2,157,887 | 5/1939 | Davis | 242/47.5 UX |
| 2,466,996 | 4/1949 | Monnot | 242/47.5 |
| 2,482,851 | 9/1949 | Jennewein | 242/47.5 X |
| 2,560,204 | 7/1951 | Andren | 242/47.5 X |
| 2,730,183 | 1/1956 | Svoboda | 242/47.5 X |
| 2,896,659 | 7/1959 | Erickson | 242/47.5 X |
| 2,944,748 | 7/1960 | Carnagua et al. | 242/47.5 |
| 3,180,585 | 4/1965 | Pusey et al. | 242/47.5 |
| 3,429,516 | 2/1969 | Sharp et al. | 242/47.5 |

FOREIGN PATENT DOCUMENTS 442556  2/1936  United Kingdom .................... 242/47.5

Primary Examiner—Stanley N. Gilreath
Attorney, Agent, or Firm—Burd, Braddock & Bartz

[57] ABSTRACT

A sterile surgical cord and tube retractor for use by surgeons while operating to maintain accessories, such as suction tubes and cauterizing forceps, within easy reach of the surgeon without obstructing the surgical field with tubing and cord when not in use. The device comprises a housing adapted to be supported on the usual instrument table positioned adjacent the surgical field, and in turn supports the instrument tray. A plurality of spring tensioned retractors within the housing separately hold lengths of tubing and cord, permitting them to be withdrawn from the housing for use and then retracted back into the housing.

4 Claims, 8 Drawing Figures

U.S. Patent Nov. 20, 1979 Sheet 1 of 3 4,174,816
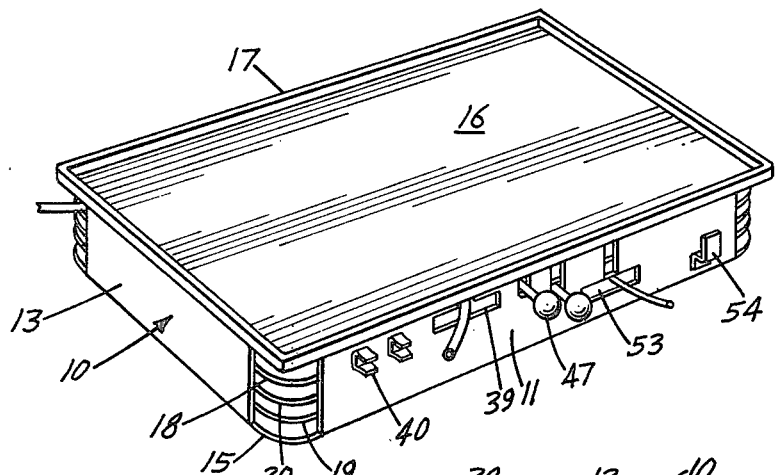
Fig. 1
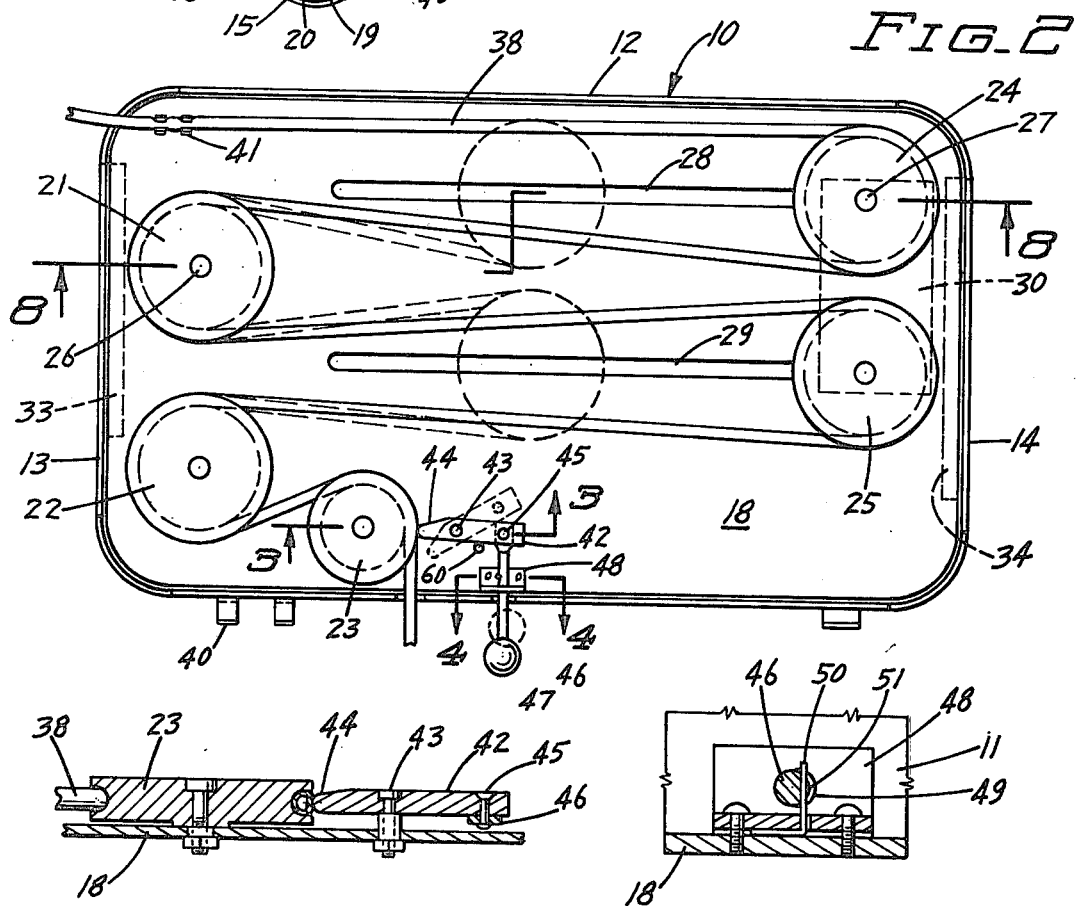
Fig. 2
Fig. 3
Fig. 4

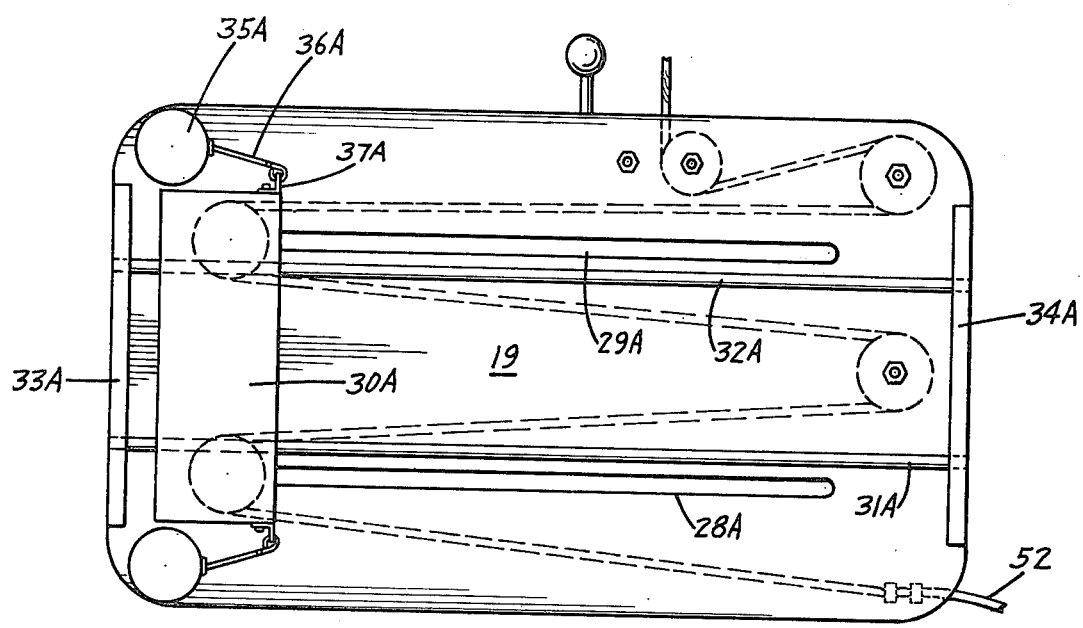
FIG_7
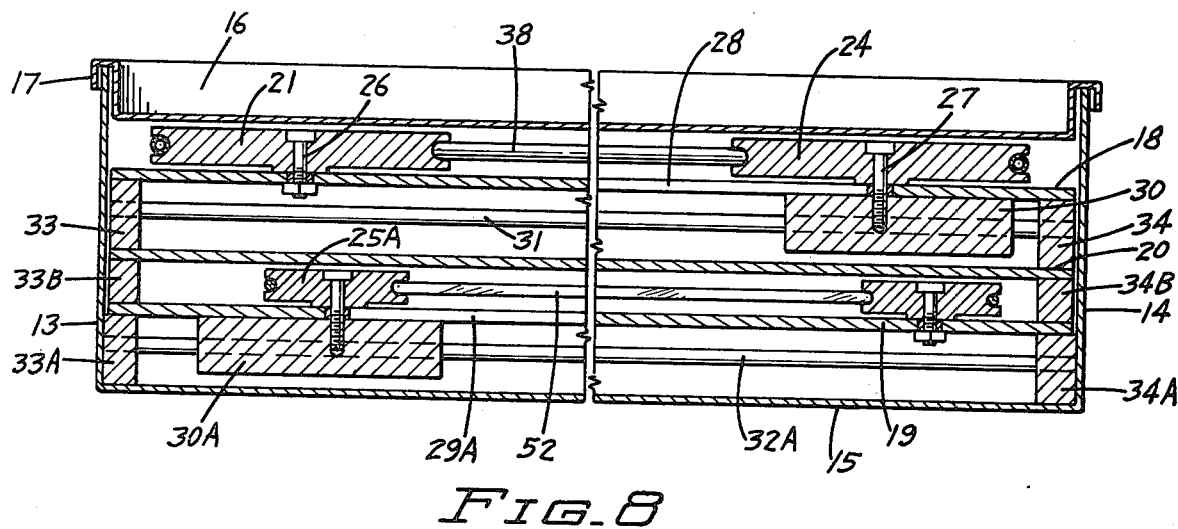
FIG_8

STERILE SURGICAL CORD AND TUBE RETRACTOR

This invention relates to a retractor for storing elongated flexible linear elements, such as cord and tubing, available to be withdrawn for use and then retracted back into the storage area. More particularly, this invention relates to a sterile surgical cord and tube retractor for use by surgeons in the operating room while performing surgery.

During surgery electrical cautery forceps are used to close small blood vessels to inhibit the flow of blood into the surgical field. Suction devices are employed to remove blood and other fluids from the field to give the surgeon an unobstructed view. The surgical nurse is normally charged with responsibility for manipulating the connecting cords and tubes during the surgical procedure to keep them out of the way of the surgeon. Because of their length, there is a constant possibility of contamination of the cords and tubes from falling off the surgical field. The retractor of the present invention is directed to the elimination of these problems and generally facilitates use of auxiliary devices during the surgical procedure.

These results are accomplished by removing all unused cords and tubes from the surgical area when not in immediate use. At the same time, the cords and tubes are stored and readily accessible for use when needed, without contamination. The retractor takes up no space in the operating field and releases the surgical nurse from the duty of manipulating cords and tubes, as well as eliminating the possibility of contamination from falling off the surgical field.

The invention is illustrated in the accompanying drawings in which:

FIG. 1 is a perspective view of the cord and tube retractor;

FIG. 2 is a top plan view of the retractor unit shown with the top instrument tray removed and exposing a suction tube retractor plate within the housing;

FIG. 3 is a fragmentary section on an enlarged scale taken on the line 3—3 of FIG. 2 and in the direction of the arrows showing details of braking means for holding a tube in extended position for use;

FIG. 4 is a fragmentary vertical section on a further enlarged scale taken on the line 4—4 of FIG. 2 and in the direction of the arrows and showing further details of the braking structure;

FIG. 7 is a bottom plan view of the plate of FIG. 6; and

FIG. 8 is a composite longitudinal elevation in section of the cord and tube retractor, the top half of the view being through the tube supporting retractor plate and taken on the line 8—8 of FIG. 2 and in the direction of the arrows, and the bottom half of the view being through the cord supporting retractor plate and taken on the line 8A—8A of FIG. 6 and in the direction of the arrows.

Figure 5:
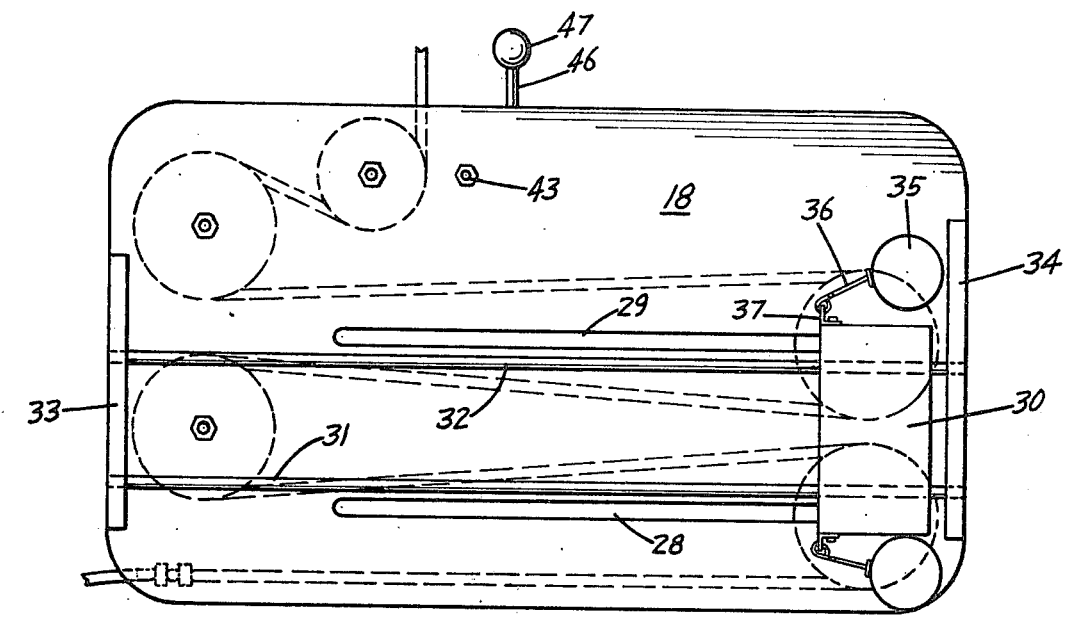
FIG. 5 is a bottom plan view of the suction tube retractor plate.

Referring to the drawings, the cord and tube retractor comprises a housing indicated generally at 10 and having a front wall 11, back wall 12, end walls 13 and 14 and bottom wall 15. For convenience in assembly, disassembly and for sterilizing, the corners of the housing are desirably left open, as best seen in FIG. 1. An instrument tray 16 serves as a removable top wall for the housing. Tray 16 is preferably provided with a continuous flange 17 around its periphery for engagement with the top edges of the front, back and end walls of the housing. The retractor housing 10 is adapted to set on top of the standard movable surgical stand, referred to as the Mayo stand, which is adapted to fit over the patient on the operating table so that the instruments thereon are within easy reach of the surgeon. The top tray 16 of the retractor is used to hold the surgical instruments that otherwise would be on the Mayo stand.

Within the housing are a plurality of stacked spaced apart parallel horizontal plates. The top-most of these, tube retractor plate 18, is adapted to hold a length of hollow tubing. The bottom-most of the plates, cord retractor plate 19, is adapted to hold a length of electrical cord. A spacer or separator plate 20 separates the tube plate from the cord plate. Although the retractor is shown as having two plates, one intended to accommodate suction tubing and the other to accommodate electrical cord for cauterizing forceps, the apparatus is adaptable to contain additional plates for other linear cord and tubing elements according to the requirements and desires of the surgeon, such as additional lighting, gas supply lines, etc.

Referring now to FIGS. 2 and 5, the suction retractor plate 18 on its upper surface supports a plurality of horizontally disposed, peripherally grooved wheels or pulleys disposed on the top surface of the plate and journaled to rotate on parallel vertical axes. Pulleys 21, 22 and 23 are in fixed positions, each being journaled to rotate on a stub shaft 26 secured in plate 18. Pulleys 24 and 25 are movable, each being journaled on a stub shaft 27 extending through one of longitudinal slots 28 and 29 and secured to a trolley block 30 on the underside of plate 18. Trolley block 30 in turn is mounted for reciprocable movement along a pair of longitudinal rods 31 and 32 whose opposite ends are supported, spaced slightly below the bottom surface of plate 18, in a pair of end spacer bars 33 and 34 which are secured to the bottom surface of plate 18 adjacent the opposite ends thereof. Thus, pulleys 24 and 25 are mounted for reciprocation longitudinally across the top of plate 18 toward fixed pulleys 21 and 22, being guided by slots 28 and 29.

Trolley block 30 is resiliently tensioned so as to maintain a normal at-rest position at the end of plate 18 remote from fixed pulleys 21 and 22. In this instance, the tensioning means comprises a pair of encased spiral coil or clock springs 35 each fixed to plate 18 and connected to block 30 by means of a flexible tape, cord or chain 36 whose free end is connected to block 30 at bracket 37. Although movable pulleys 24 and 25 are shown mounted for movement together, optionally they may be separately mounted for independent movement by the use of a pair of trolley blocks mounted, guided and tensioned similar to block 30.

Suction tube 38 is introduced into the housing, through the open left rear corner, as illustrated (FIG. 2), and threaded in a serpentine path around movable pulley 24, fixed pulley 21, movable pulley 25, fixed pulley 22 and fixed pulley 23 and thence out through opening 39 in the front wall 11 of the housing. Sufficient tubing 38 is initially disposed around the pulleys and through opening 39 to permit attachment of a suitable suction accessory tool to the free end. A pair of spring clamps 40 are desirably also affixed to the outside of front wall 11 for holding that tool when not in use.

An anchoring means, in this instance a spring clip 41, is affixed to the top surface of plate 18 so as to anchor the suction tubing adjacent its point of entry into the retractor housing. This fastening means must hold the tubing sufficiently firmly that, when the tubing is passed in its serpentine path around the pulleys, it will resist pulling tension on the tubing as it is withdrawn from the housing to the surgical field to cause the desired reciprocable movement of movable pulleys 24 and 25. The tubing following the serpentine path around the pulleys represents the amount of tubing stored within the housing, most of which is available for extension to permit the surgeon considerable latitude in his movement of the suction tool in and around the surgical field.

It will be readily seen that pulling tension exerted on the free end of tubing 38 is transmitted by the tubing itself around pulleys 23 and 22 to movable pulley 25. Because of the resilient mounting of pulley 25, and the fact that the tubing is anchored at its point of entry, the transmitted force urges that pulley to move along slot 29 shortening the serpentine path and making available that additional length of tubing outside of the housing. Because pulleys 24 and 25 are desirably mounted to move together, additional foreshortening of the serpentine path occurs as a result of movement of pulley 24. The suction tube may be withdrawn from the housing with only slightly increasing tension. When the suction tool is no longer needed, the tubing is retracted automatically as the tool is returned to its retaining clips 40.

In order that the surgeon need not maintain tension on the tube as it is in use, a braking structure is provided, as best seen in FIGS. 2, 3 and 4. The brake comprises a bar 42 pivotally attached at 43 to the top surface of plate 18 for slight rotation in a horizontal plane parallel to and spaced slightly from the upper surface of plate 18. Bar 42 is pivoted off-center. One end is provided with a snub-nose 44 adapted in braking position to engage and compress the outer wall only of the flexible tubing 38 as it is engaged in the groove of fixed pulley 23 sufficient to restrain that pulley from further rotation.

The opposite end of bar 42 is pivotally attached at 45 to one end of a lever arm 46 which extends through the front housing wall 11 and is provided with a knob or handle 47 at its free end. The brake arm 42 operates on a push-pull basis. Pushing on knob 42 moves the brake arm to inoperative position whereas pulling on the knob actuates the brake. Arm 46 extends through the opening 49 in angle bracket 48 which is secured to the top surface of plate 18 immediately adjacent the inside wall surface of housing front wall 11. Angle bracket 48 supports a vertical spring pin 50 which extends upwardly from the horizontal portion of the angle plate and is positioned to engage a notch 51 in the side of arm 48 to maintain the brake in operative braking position. A vertical stop pin 60 limits the movement of the brake bar 42 and likewise assists in maintaining it in operative position.

The bottom surface of instrument tray 16 is closely spaced from the top surfaces of pulleys 21–25 so as to insure against escape of the tubing from the pulley grooves. The end spacer bars 33 and 34 of suction tubing plate 18 rest upon the top surface of separator plate 20. Separator plate 20 in turn is provided with end spacer bars 33B and 34B which rest upon the top surface of cord retractor plate 19. Plate 19 in turn is provided with end spacer bars 33A and 34A which in turn rest upon the top surface of bottom wall 15 of the housing.

Figure 6:
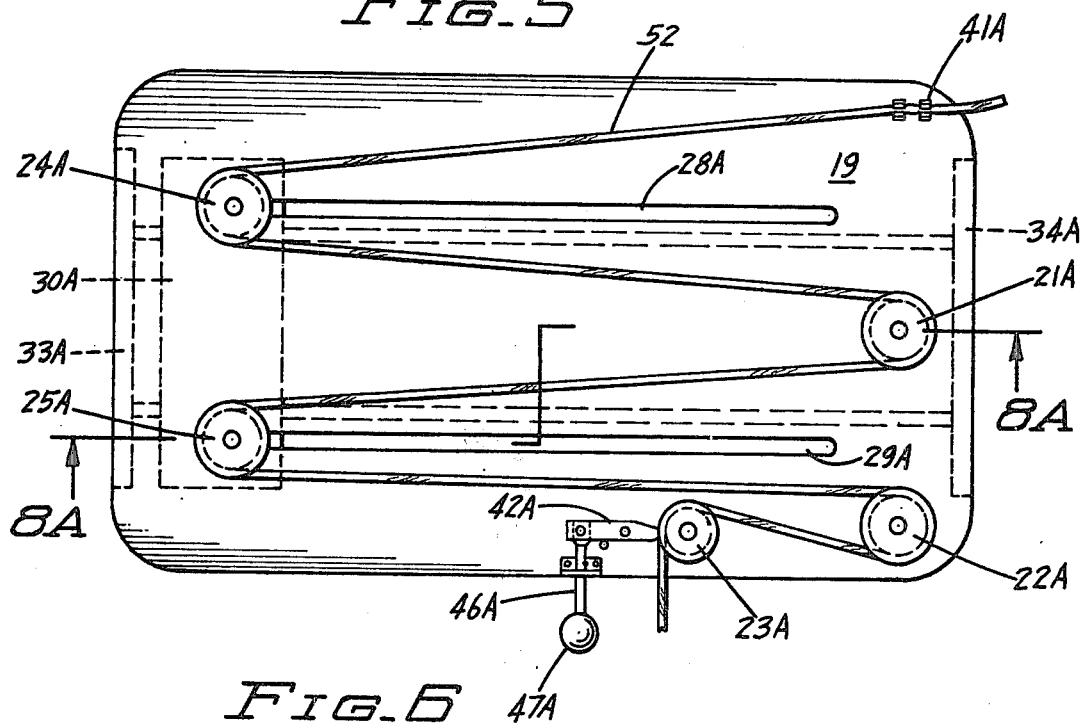
FIG. 6 is a top plan view of a plate for retractably supporting a length of electrical cord.

The structure of the cord retractor plate as shown in FIGS. 6 and 7 is generally similar to that of the suction tubing plate, but disposed in mirror image thereof. Corresponding numerals identify corresponding parts of the cord plate with the addition of suffix A. Thus, cord 52 adjacent its entry to the housing is anchored by spring clips 41A and passes in a serpentine path around movable pulley 24A, fixed pulley 21, movable pulley 25A, fixed pulley 22A and fixed pulley 23A and thence out through opening 53 in the front housing wall 11. A clip 54 is provided on the outside surface of front wall 11 for holding cauterizing forceps or similar instruments.

Movable pulleys 24A and 25A are mounted on trolley block 30A for movement along the track formed by rods 31A and 32A guided by longitudinal slots 28A and 29A. Tension is exerted against block 30A as described with reference to the suction tubing plate. The braking structure 42A–47A is likewise generally as described in connection with the suction tubing plate, apart from being in mirror image with respect thereto. Separator plate 20 is closely spaced from the top surfaces of pulleys 21A–25A to retain the cord in the pulley grooves. The electrical cord 52 may be withdrawn, locked in position by operation of the braking structure and retracted in the same manner already described in connection with the suction tubing. Each cord or tube, having its own set of trolleys and pulleys independent of the others, can be used independently of the other.

The retractor apparatus is designed for easy assembly and disassembly. Cord and tubing is easily removed for cleaning and sterilizing or replacement and easily rethreaded around the pulleys of the appropriate retractor plate. The reassembled unit can be rendered sterile by autoclaving or gas sterilization. The retractor housing and plates may desirably be formed from aluminum and/or stainless steel. The grooved wheels or pulleys are desirably formed from nylon, as is the braking bar. The spacer bars and trolley blocks may be metallic or non-metallic as desired so long as they are capable of easy cleaning and sterilization. The trolley rods are desirably formed from stainless steel.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. A retractor for elongated flexible linear tube and cord elements used in surgical procedures, said retractor comprising:
 (A) a horizontally disposed housing having vertical end walls and side walls and a removable top tray,
 (B) a plurality of stacked horizontal parallel vertically spaced apart retractor plates within said housing,
 (C) a plurality of laterally spaced apart peripherally grooved wheels fixedly mounted on the top side of each of said retractor plates adjacent one end thereof, said wheels being journaled for rotation about vertical axes,
 (D) a plurality of laterally spaced apart peripherally grooved wheels movably mounted on the top side of each of said retractor plates adjacent the opposite end thereof for reciprocable movement relative to said fixedly mounted wheels, said wheels being journaled for rotation about vertical axes, (E) a plurality of longitudinal slots in each of said retractor plates in number corresponding to said reciprocable wheels, said reciprocable wheels being mounted for movement in said slots, (F) resilient tension means connected to said reciprocable wheels for normally urging said wheels away from said fixedly mounted wheels, (G) a further peripherally grooved wheel fixedly mounted on the top side of each of said retractor plates adjacent one side edge of said plate between the first mentioned fixedly mounted wheels and reciprocable wheels, (H) a first opening in said housing for entry of a linear element to each of said retractor plates, (I) fastening means on each of said retractor plates adjacent said entry opening for securing a linear element to each plate, whereby, when said linear element is threaded in a serpentine path around said reciprocable and fixedly mounted wheels, said fastening means resists pulling tension on the free end of said element sufficient to cause movement of the reciprocable wheels toward the fixedly mounted wheels resulting in shortening of the serpentine path and extension of the element, and (J) a further exit opening in said housing adjacent each said further fixedly mounted wheel.

2. A retractor according to claim 1 further characterized in that braking means are mounted on each of said retractor plates adjacent to each said further fixedly mounted wheel, each said braking means comprising:

(A) a braking element engageable with the peripheral groove of said further wheel, and (B) handle means extending to the exterior of said housing for moving said braking element into and out of engagement with said respective wheel.

3. A retractor according to claim 1 further characterized in that:

(A) said reciprocable wheels for each retractor plate are movable together, (B) a pair of parallel horizontal rods are mounted below each retractor plate closely spaced therefrom and parallel thereto, (C) a trolley block is supported on each pair of said rods for slideable movement therealong, (D) each of said reciprocable wheels for each retractor plate is mounted for rotation on a stub shaft extending through one of said parallel slots into said trolley block, and (E) said resilient tension means is connected to said wheels through said trolley block.

4. A retractor according to claim 1 further characterized in that a separator plate is disposed within said housing between each pair of retractor plates, said separator plate being parallel to the retractor plates and closely spaced from the grooved wheels of the next underlying retractor plate to prevent dislodgment of the linear element therefrom.

* * * * *